United States Patent
Zhao et al.

(10) Patent No.: US 10,729,713 B2
(45) Date of Patent: Aug. 4, 2020

(54) PHARMACEUTICAL COMPOSITION FOR TREATING HEPATITIS, LIVER FIBROSIS, AND LIVER CANCER

(71) Applicant: GUANGDONG PROVINCIAL HOSPITAL OF CHINESE MEDICINE, Guangzhou, Guangdong (CN)

(72) Inventors: Ruizhi Zhao, Guangdong (CN); Ya Zhao, Guangdong (CN); Lijuan Liu, Guangdong (CN)

(73) Assignee: GUANGDONG PROVINCIAL HOSPITAL OF CHINESE MEDICINE, Guangzhou, Guangdong (CN)

( * ) Notice: Subject to any disclaimer, the term of this patent is extended or adjusted under 35 U.S.C. 154(b) by 0 days.

(21) Appl. No.: 16/087,624

(22) PCT Filed: Mar. 24, 2017

(86) PCT No.: PCT/CN2017/078050
§ 371 (c)(1),
(2) Date: Sep. 21, 2018

(87) PCT Pub. No.: WO2017/181816
PCT Pub. Date: Oct. 26, 2017

(65) Prior Publication Data
US 2019/0099439 A1    Apr. 4, 2019

(30) Foreign Application Priority Data

Apr. 21, 2016  (CN) .......................... 2016 1 0255001

(51) Int. Cl.
*A61K 36/233* (2006.01)
*A61K 31/715* (2006.01)
*A61K 31/4375* (2006.01)
*A61P 35/00* (2006.01)
*A61P 1/16* (2006.01)

(52) U.S. Cl.
CPC ........ *A61K 31/715* (2013.01); *A61K 31/4375* (2013.01); *A61K 36/233* (2013.01); *A61P 1/16* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 2002/0102237 A1* | 8/2002 | Hammerly | A61K 36/28 424/85.5 |
| 2012/0034238 A1* | 2/2012 | Chen | A61K 35/57 424/161.1 |
| 2013/0158097 A1* | 6/2013 | Hinkle | C12N 15/113 514/44 A |

FOREIGN PATENT DOCUMENTS

| | | | |
|---|---|---|---|
| CN | 1706474 A | | 12/2005 |
| CN | 101129974 | * | 8/2007 |
| CN | 101612179 | * | 12/2009 |

OTHER PUBLICATIONS

Zhao R. et al. Liver Targeting Effect of Vinegar Baked Radix Bupleuri on Oxymatrine in Mice. 2011 IEEE Int Conference, 740-745, 2011. (Year: 2011).*
Zhao, R. Target Delivery in Traditional Chinese Medicine. Drug Metabolism Reviews 43(Suppl 2)96-97, Abstract #P123, Nov. 2011. (Year: 2011).*
Kwon, H. et al. Heptatits B Therapy. Nature Reviews: Gastroenterology & Hepatology 8:275-284, May 2011. (Year: 2011).*
Chen, Youjun, "Study on Liver Targeting Effect of Vinegar Processing Radix Bupleuri on Oxymatrine in Mice", Medicine & Public Health, Chin A Master's Theses Full-Text Database, No. 10, Oct. 15, 2009 (Oct. 15, 2009), ISSN: 1674-0246, p. E057-241.
Xu, Jingyun et al., "Introduction of Treatment of B-hepatitis Kidney", Guangming Journal of Chinese Medicine, vol. 25, No. 3, Mar. 31, 2010 (Mar. 31, 2010), ISSN:1003-8914, p. 394.

* cited by examiner

*Primary Examiner* — Ralph J Gitomer
(74) *Attorney, Agent, or Firm* — Global IP Services; Tianhua Gu

(57) ABSTRACT

The present invention relates to a pharmaceutical composition for treating hepatitis, liver fibrosis, and liver cancer, which comprises the following components in parts by weight: 0.15-10 parts of vinegar-baked *bupleurum* root polysaccharides or *bupleurum* root polysaccharides and 0.05-5 parts of a drug for treating hepatitis.

6 Claims, No Drawings

PHARMACEUTICAL COMPOSITION FOR TREATING HEPATITIS, LIVER FIBROSIS, AND LIVER CANCER

CROSS REFERENCE TO RELATED PATENT APPLICATION

The present application is the US national stage of PCT/CN2017/078050 filed on Mar. 24, 2017, which claims the priority of the Chinese patent application No. CN201610255001.X filed on Apr. 21, 2016, which application is incorporated herein by reference.

BACKGROUND OF THE PRESENT INVENTION

Field of Invention

The present invention relates to a composition comprising *bupleurum* root polysaccharides and use thereof in the prevention and treatment of hepatitis and liver cancer.

Description of Related Arts

Hepatitis B is a disease caused by Hepatitis B Virus (HBV) that seriously harms human health. At present, there are approximately 350 million people in the world are carriers of HBV, and there are approximately 120 million HBsAg-positive patients in China. Persistent infection with HBV will lead to liver diseases such as cirrhosis and primary hepatocellular carcinoma, and the mortality rate is high. WHO has listed Hepatitis B as the ninth cause of death in the world. Although the Hepatitis B vaccine has been widely used, which can effectively prevent Hepatitis B to some extent, problems such as non-response and adverse reactions still exist. The studies have found that 60-70% of the liver biopsies of "asymptomatic HBV carriers" show chronic persistent hepatitis or chronic active hepatitis, and long-term infection with Hepatitis B virus can be developed into liver cirrhosis, even liver cancer. Therefore, anti-HBV treatment to prevent the further development of the disease is critical, and the research and development of new drugs with good antiviral effect and low side effects have become an urgent task in the medical field today.

The existing drugs for treating Hepatitis B mainly include interferons, nucleoside drugs, and oxymatrine. Among them, interferon needs to be administered by injection, which is inconvenient in use; and oxymatrine and nucleosides can be taken orally, and thus the patient's compliance is higher. However, the above drugs cannot kill the virus, but inhibit its replication only. Therefore, at least six months are needed for the treatment. The nucleoside drugs are widely distributed in the body, and the patients often suffer from toxic reactions such as nausea and vomiting. Long-term use of the nucleoside drugs may lead to serious adverse reactions such as anemia and fatigue due to the inhibition on the bone marrow hematopoietic system. Oxymatrine has limited efficacy due to the wide distribution. Therefore, how to increase the concentration at the target site to improve the efficacy, reduce the distribution in extrahepatic tissues, and reduce the toxic side effects has become a hotspot in pharmaceutical research.

At present, the studies on the liver targeting of anti-hepatitis B drugs mainly include the following approaches: (1) modifying anti-HBV drugs with monophosphorylation, wherein compared with the control group, the concentration of Lamivudine in the liver can be increased by 7.7 times, and the AUC is increased by 11.2 times; (2) grafting biological macromolecules with higher affinity on the liver to target the liver; and (3) preparing a passively targeted liver microparticle preparation. The above methods can achieve ideal results in laboratory studies. However, because the research methods have many steps, complicated routes, difficulty in process quality control, and expensive materials, as well as the need for organic solvents, industrial production still faces enormous difficulties. Therefore, it is critical in the treatment of hepatitis B to find a suitable liver-targeted drug delivery system.

SUMMARY OF THE PRESENT INVENTION

An object of the present invention is to provide a traditional Chinese medicine composition for treating hepatitis and liver cancer, to meet the needs in clinical applications.

The traditional Chinese medicine composition for treating hepatitis and liver cancer according to the present invention comprises the following components in parts by weight:

0.15-10 parts of vinegar-baked *bupleurum* root polysaccharides or *bupleurum* root polysaccharides, which is equivalent to 3-60 parts of vinegar-baked raw *bupleurum* root; and 0.05-5 parts of a drug for treating hepatitis.

The drug for treating hepatitis is selected from oxymatrine, matrine, Lamivudine or a structural analogue thereof, Adefovir Dipivoxil, Entecavir, Telbivudine, and Tenofovir.

Preferably, the traditional Chinese medicine composition comprises the following components in parts by weight:

0.05-2 parts of oxymatrine or matrine; and 0.5-5 parts of vinegar-baked *bupleurum* root polysaccharides or *bupleurum* root polysaccharides, which is equivalent to 10-60 parts of vinegar-baked raw *bupleurum* root.

Preferably, the traditional Chinese medicine composition comprises the following components in parts by weight:

0.05-1 part of oxymatrine or matrine; and 0.5-5 parts of vinegar-baked *bupleurum* root polysaccharides, which is equivalent to 10-60 parts of vinegar-baked raw *bupleurum* root;

Preferably, the traditional Chinese medicine composition comprises the following components in parts by weight:

0.020-0.1 part of Lamivudine; and 0.5-5 parts of *bupleurum* root polysaccharides, which is equivalent to 10-60 parts of raw *bupleurum* root.

Preferably, the traditional Chinese medicine composition comprises the following components in parts by weight:

0.010-0.1 part of Adefovir Dipivoxil; and 0.15-5 parts of vinegar-baked *bupleurum* root polysaccharides, which is equivalent to 8-50 parts of vinegar-baked raw *bupleurum* root.

Preferably, the traditional Chinese medicine composition comprises the following components in parts by weight:

0.010-0.1 part of Entecavir; and 0.5-5 parts of vinegar-baked *bupleurum* root polysaccharides, which is equivalent to 8-50 parts of vinegar-baked raw *bupleurum* root.

Preferably, the traditional Chinese medicine composition comprises the following components in parts by weight:

0.005-0.1 part of Telbivudine; and 0.5-5 parts of *bupleurum* root polysaccharides, which is equivalent to 10-60 parts of raw *bupleurum* root.

Preferably, the traditional Chinese medicine composition comprises the following components in parts by weight:
0.005-0.1 part of Tenofovir; and
0.5-5 parts of *bupleurum* root polysaccharides, which is equivalent to 10-60 parts of vinegar-baked raw *bupleurum* root.

Most preferably, the traditional Chinese medicine composition comprises the following components in parts by weight:
0.05-2 parts of oxymatrine or matrine; and
0.84 part of vinegar-baked *bupleurum* root polysaccharides, which is equivalent to 16.8 parts of vinegar-baked raw *bupleurum* root.

The oxymatrine is a commercially available synthetic or natural extracted product with a purity of ≥80%.

The *bupleurum* root is the root of *Bupleurum Chinese* DC and *Bupleurum scorzonerifolium Willd*, which is commonly used to treat flu, fever, scars, hepatitis, jaundice, nephritis, lung diseases, cancers, bitterness in the mouth and irregular menstruation.

The vinegar-baked *bupleurum* root is a medicine obtained by drying and sectioning the *bupleurum* root, spraying and fully impregnating with vinegar, and stir-heating slightly with mild fire.

Animal experiments have proved that the traditional Chinese medicine composition for treating hepatitis and liver cancer according to the present invention has obvious therapeutic effects in the treatment of hepatitis and liver cancer, and can be used for preparing drugs for treating hepatitis and liver cancer.

The present invention also relates to a traditional Chinese medicine preparation for treating hepatitis and liver cancer, which comprises a therapeutically effective amount of the traditional Chinese medicine composition for treating hepatitis and liver cancer, and a pharmaceutically acceptable carrier, such as a flavoring agent, a sweetener, a liquid or solid filler or diluents, and other commonly used carrier materials, which are prepared into the traditional Chinese medicine preparation for treating hepatitis and liver cancer by methods well known in the art. The preparation comprises an emulsion, tablets, granules, an oral liquid, capsules, dripping pills, pills, and injections, etc.

A preparation method according to the present invention comprises the following steps:

(1) Preparation of Vinegar-Baked *Bupleurum* Root Polysaccharides 60 parts of (vinegar-baked) *bupleurum* root is added to water that is 10 times the weight of the (vinegar-baked) *bupleurum* root, soaked for 20-50 min, boiled for 20-50 min, filtered, and boiled for another 30 min. The filtrates are combined, concentrated, cooled, added with absolute ethanol to give a volume fraction of ethanol of 80%, and then stood at room temperature for 12-24 hrs. The suspension is centrifuged for 5 min at 4000 r/min. The pellet is the crude polysaccharides from vinegar-baked *bupleurum* root, which may be decolored, and removed of the proteins to get the refined polysaccharides.

(2) The drug for treating hepatitis is added to the crude polysaccharides or refined polysaccharides and mixed to obtain the traditional Chinese medicine composition for treating hepatitis and liver cancer.

(3) A carrier is added to the product of Step (2), and then prepared into the traditional Chinese medicine preparation for treating hepatitis and liver cancer through a method well known in the art.

The present invention can be administered to patients in need of treatment by oral or injection route, and the dose is generally 4.8 to 10 mg/kg body weight per day (oxymatrine, matrine, Lamivudine, Telbivudine), 0.005-0.01 mg/kg body weight per day (Entecavir), and 2-5 mg/kg body weight per day (Adefovir Dipivoxil, or Tenofovir), which may be decided by a physician depending on the specific conditions of the patient.

In the present invention, an anti-hepatitis hepatoprotective drug and a liver meridian guiding drug comprising (vinegar-baked) *bupleurum* root polysaccharides as a main active ingredient are combined into a pharmaceutical preparation for treating hepatitis and liver cancer, in which the latter can delay the drug metabolism, prolong the retention time, and increase the intake in liver, thus improving the efficacy.

In the present invention, the raw medicine oxymatrine and its metabolite matrine have the effects of anti-cancer, anti-inflammatory, antipyretic and analgesic, anti-arrhythmia, immune regulation, anti-virus, liver protection, anti-liver fibrosis, and other pharmacological effects. Lamivudine and its analogues such as Adefovir Dipivoxil, Entecavir, Telbivudine, and Tenofovir can inhibit the replication of hepatitis virus and prevent hepatic fibrosis and liver cancer, and have been clinically used in the treatment of cancers and in the protection of liver. Lamivudine and its analogues HAVE obvious anti-HBV effect, but are widely distributed in the body, causing side effects such as nausea, vomiting, bone marrow suppression and anemia. Oxymatrine is limited in its efficacy in the treatment of hepatitis, liver fibrosis, and liver cancer, due to the wide distribution in body. Vinegar-baked *bupleurum* root is a processed product of *bupleurum* root, which can increase the glutathione level in liver, reduce the content of liver collagen, and promote the proliferation of hepatocytes, thus exerting a liver protection effect; which can regulate INF-γ factors, thus having anti-inflammatory effects; and which is commonly used to treat liver cirrhosis, hepatic fibrosis and other liver diseases in modern medicine. The vinegar-baked *bupleurum* root is mainly tropic to liver meridian is a liver meridian guiding drug. The vinegar-baked *bupleurum* root polysaccharides are obtained after the extraction and separation. The vinegar-baked *bupleurum* root polysaccharides have the anti-radiation effect, the effects of lowering blood lipid and enhancing the immune function, the antiviral effect, and strong anti-ulcer effect, and have significant clinical benefits for hepatitis and systemic lupus erythematosus, nephritis, rheumatoid arthritis and other autoimmune diseases. Experimental studies show that vinegar-baked *bupleurum* root polysaccharides can increase the distribution and prolong the action time of oxymatrine in the liver, thereby enhancing its efficacy.

The present invention has the following beneficial effects.

The vinegar-baked *bupleurum* root polysaccharides can significantly increase the intrahepatic distribution of drugs for treating hepatitis, and enhance the activity of these drugs against hepatitis virus and against hepatitis and liver cancer. Moreover, the vinegar-baked *bupleurum* root polysaccharides also can reduce the distribution of drugs for treating hepatitis in the gastrointestinal tract, bone marrow, muscle and other tissues, and are expected to reduce the adverse reactions such as nausea, vomiting, anemia, bone marrow suppression, fatigue and others.

DETAILED DESCRIPTION OF THE PREFERRED EMBODIMENTS

The present invention is described in further detail below by way of examples. The examples are provided to illustrate, instead of limiting the scope of the present invention.

Example 1

Composition:

60 parts of *bupleurum* root, 5 parts of oxymatrine (purity ≥80%), and 20 parts of starch Preparation Method The *bupleurum* root is weighed and added to water, the weight of the water is 10 times the weight of the *bupleurum* root, soaked for 30 min, then boiled, and simmered for 30 min, filtered with gauze, and boiled for another 30 min. The filtrates is combined, concentrated, cooled, added with absolute ethanol to give a volume fraction of ethanol of 80%, and then stood at room temperature for 24 h. The suspension is centrifuged for 5 min at 4000 r/min. The pellet is the *bupleurum* root polysaccharides (PSS). Oxymatrine and starch are added to the pellet, after that the pellet is prepared into tablets through a method well known in the art.

Example 2

Composition 3 parts of vinegar-baked *bupleurum* root, 5 parts of oxymatrine (purity ≥80%), and 10 parts of microcrystalline cellulose;

Preparation Method:

Following the method described in Example 1, vinegar-baked *bupleurum* root is weighed, extracted with water and precipitated in ethanol. The precipitate was collected by centrifugation, added with oxymatrine and microcrystalline cellulose, and then prepared into capsules through a method well known in the art.

Example 3

Composition 10 parts of *bupleurum* root, 1 part of Lamivudine, and 5 parts of lactose. The preparation method is the same as that in Example 1.

Example 4

15 parts of vinegar-baked *bupleurum* root, 0.5 part of Adefovir Dipivoxil, and 1 part of lactose. The preparation method is the same as that in Example 1.

Example 5

50 parts of *bupleurum* root, 2 parts of Entecavir, and 5 parts of microcrystalline cellulose. The preparation method is the same as that in Example 1.

Example 6

40 parts of vinegar-baked *bupleurum* root, 1.5 parts of Telbivudine, and 15 parts of microcrystalline cellulose. The preparation method is the same as that in Example 1.

Example 7

35 parts of vinegar-baked *bupleurum* root, 2 parts of Tenofovir, and 10 parts of microcrystalline cellulose. The preparation method is the same as that in Example 1.

Example 8

The pharmaceutical composition of the present invention enhances the distribution of oxymatrine (OM) in the rat liver.

36 rats are acclimated for 7 days, and randomized into a treatment group with oxymatrine (OM) alone, and a treatment group with a combined drug of the present invention (drug in Example 1).

Wherein, the dosage of oxymatrine (OM) is 54 mg/kg, and the *bupleurum* root polysaccharides are used at a corresponding dosage in Example 1. After a single administration, blood is sampled from the abdominal aorta respectively at 20 min, 60 min, and 240 min. The rat is sacrificed, from which the liver, spleen, lung, kidney, and heart are removed. The blood is wiped off with filter paper, and the adipose tissue is removed. 0.1 mL of serum is extracted with chloroform and blow dried with nitrogen, and the residue is dissolved in 0.1 mL of methanol and used as a test solution. The tissue sample is accurately weighed, added with physiological saline at a ratio of 1:10, and homogenized. 0.2 mL of the homogenate is taken, and treated following method the same as the blood sample. The concentrations of oxymatrine (OM) and its metabolite (M) are determined by LC-MS, the content in the tissue and the area under the curve are calculated. The results are shown in Tables 1 and 2 below.

TABLE 1

AUC results of oxymatrine (μg/L*h, n = 6)

| Group | Plasma | Tissue | | | | |
| --- | --- | --- | --- | --- | --- | --- |
| | | Liver | Spleen | Lung | Kidney | Heart |
| OM | 520.50 | 125.02 | 64.94 | 365.52 | 69.66 | 125.35 |
| OM + PSS | 253.96 | 163.82 | 34.79 | 439.25 | 72.08 | 111.47 |

TABLE 2

AUC results of matrine (μg/L*h, n = 6)

| Group | Plasma | Tissue | | | | |
| --- | --- | --- | --- | --- | --- | --- |
| | | Liver | Spleen | Lung | Kidney | Heart |
| OM | 15253.01 | 3611.03 | 6402.53 | 6448.48 | 5602.98 | 1963.81 |
| OM + PSS | 8221.87 | 2808.82 | 3496.18 | 2521.83 | 3506.81 | 1256.42 |

As calculated, the rates of targeting to liver of OM, M and the two in combination are 2.37, 1.42, and 1.46 times, respectively. The result indicates that the *bupleurum* root polysaccharides (PSS) can significantly increase the distribution of orally taken oxymatrine preparations in the liver, thereby exerting a better liver protection effect.

Example 9

The pharmaceutical composition of the present invention enhances the Lamivudine level in the rat liver.

Grouping of the test animals and administration are the same as the Example 1 (except that the drug used is the same as Example 3). The dosage of Lamivudine is 15 mg/kg, and the *bupleurum* root polysaccharides are at a corresponding dosage.

The Lamivudine content was determined by liquid chromatography. 0.1 mL of plasma is added with 10 μL of 0.2 mol ammonium acetate, and then with 1 mL of acetonitrile, vortexed, and centrifuged. The supernatant is collected and injected for determination. 0.1 g of the tissue sample is added with 1 mL of physiological saline, homogenized, and treated following the same method as for the plasma sample. The Lamivudine contents in the plasma and tissue sample are determined. The results are shown below.

TABLE 3

| AUC results of Lamivudine (μg/L*h, n = 6) | | | | | | | |
|---|---|---|---|---|---|---|---|
| Group | Plasma | Liver | Spleen | Lung | Kidney | Heart | Stomach |
| Lamivudine | 25.36 | 27.32 | 30.25 | 23.11 | 24.32 | 26.75 | 28.78 |
| Lamivudine + bupleurum root polysaccharides | 15.23 | 36.78 | 16.25 | 10.21 | 19.65 | 18.34 | 15.32 |

As can be seen from Table 3, the *bupleurum* root polysaccharides can significantly increase the intrahepatic distribution of lamivudine, and are expected to reduce the adverse reactions such as nausea and vomiting.

Example 10

The pharmaceutical composition of the present invention enhances the inhibition of Adefovir Dipivoxil on the replication of HBV.

The drug of Example 4 is used. The concentration of Adefovir Dipivoxil was 1 μmol, and the vinegar-baked *bupleurum* root polysaccharides are at a medium dosage in corresponding dosage, one-half of the medium dosage is a low dosage, and twice of the medium dosage is a high dosage.

The experiment is started with HepG2.215 cells that were grown to 80% confluence.

The cells were assigned to 5 groups, comprising a blank control group, a treatment group with Adefovir Dipivoxil, a treatment group with Adefovir Dipivoxil in combination with high dosage of vinegar-baked *bupleurum* root polysaccharides, a treatment group with Adefovir Dipivoxil in combination with medium dosage of vinegar-baked *bupleurum* root polysaccharides, and a treatment group with Adefovir Dipivoxil in combination with low dosage of vinegar-baked *bupleurum* root polysaccharides. Culturing for 48 h after administration, the supernatant is collected, the expression of the HBV gene is determined by fluorescent quantitative PCR, and the HBsAg and HBeAg concentrations are determined by ELISA. The results are shown in Table 4.

As can be seen from the table above, the vinegar-baked *bupleurum* root polysaccharides can significantly enhance the inhibition of adefovir dipivoxil on the replication of HBV, with the inhibition rate being increased from 60-65% to 5-10%, and the inhibition rate for gene expression being increased from 50% to nearly 90%.

Example 11

The drug of the present invention enhances the effect of Telbivudine against duck hepatitis B virus (DHBV).

The drug in Example 6 is used.

One-day-old ducklings are injected with DHBV-DNA-positive duck serum via the tibial veins (0.3 mL each), and blood is taken 7 days after infection. The serum is separated and the serum DHBV-DNA content is detected. The duckling serum is tested to be DHBV positive. Then, the ducks are randomly divided into 5 groups, comprising a virus control group, a treatment group with Telbivudine (80 mg·kg$^{-1}$), a treatment group with Telbivudine in combination with high dosage of PSS, a treatment group with Telbivudine in combination with medium dosage of PSS, and a treatment group with Telbivudine in combination with low dosage of PSS, each group has 6 ducks. The medium dosage of vinegar-baked *bupleurum* root polysaccharides is as the dosage in Example 6, the low dosage is one-half of the medium dosage, and the high dosage is twice of the medium dosage. The ducks are administered by gastric perfusion twice a day. The virus control group is given the same volume of normal saline for 10 consecutive days. Blood samples are collected from the tibial veins of the duck before administration (T0), at day 5 (T5) and day 10 (T10) of the administration, and 3 days after withdrawal (P3). The serum is separated and stored at −70° C. until test. The serum of the ducks to be tested is taken and dotted at the same time to determine the dynamics of the DHBV-DNA level in the duck serum. According to the instructions for the kit, a 32P labeled DHBV-DNA probe is used, and dot blotting is performed on the duck serum. The dot is radioactively self-developed. A value (the optical filter is at 490 nm) is determined on a microplate reader, and the absorbance of serum DHBV-DNA is calculated. The A value from dot blotting is used as the DHBV-DNA level of the specimen. The mean values of the serum DHBV-DM level in the same group of ducks before and after administration are compared, and the rates of inhibition on serum DHBV-DNA in each treatment group at various times are calculated. The results are shown in Table 5.

TABLE 4

Effect of the preparation of the present invention on replication of HBV (normalization method, 100% for control group)

| | Blank control group | Adefovir Dipivoxil | Adefovir Dipivoxil + low dosage of PSS | Adefovir Dipivoxil + medium dosage of PSS | Adefovir Dipivoxil + high dosage of PSS |
|---|---|---|---|---|---|
| HBsAg | 100 | 35 ± 1.2 | 25 ± 2.5 | 15 ± 3.6 | 5 ± 2.7 |
| HBeAg | 100 | 40 ± 3.4 | 30 ± 3.5 | 20 ± 3.2 | 10 ± 2.5 |
| Expression of HBV gene | 100 | 50 ± 5.3 | 30 ± 3.6 | 20 ± 2.5 | 11 ± 2.3 |

TABLE 5

Inhibition of the inhibitor of the present invention on the replication of HBV (normalization method, 100% for control group)

|  | Blank control group | Telbivudine | Telbivudine + low dosage of PSS | Telbivudine + medium dosage of PSS | Telbivudine + high dosage of PSS |
|---|---|---|---|---|---|
| HBsAg | 100 | 30 ± 1.3 | 21 ± 2.1 | 12 ± 2.6 | 3.6 ± 1.7 |
| HBeAg | 100 | 37.2 ± 3.4 | 28.6 ± 2.5 | 20.9 ± 2.3 | 9.5 + 1.2 |
| Expression of HBV gene | 100 | 50.5 ± 5.3 | 26.7 ± 1.3 | 19.8 ± 2.8 | 9.6 ± 1.3 |

As can be seen from Table 5, the preparation of the present invention has a good inhibitory effect on the replication of DHBV, and the result is obviously superior to telbivudine that is used alone.

Example 12

The *bupleurum* root polysaccharides enhance the distribution of Entecavir in liver, and reduce its distribution in other tissues.

The drug of Example 5 is used.

20 male mice are fasted for one night, but free accessed to water before the experiment. The animals are divided into three groups according to body weight, including a treatment group with Entecavir, and treatment groups with *bupleurum* root polysaccharides combined with Entecavir. The animals are administered for 5 consecutive days. The dosage of Entecavir is 0.1 mg/kg, and the corresponding dosage of *bupleurum* root polysaccharides in Example 5 is a high dosage, one-half of which is a low dosage. The animals are sacrificed after the last administration and the blood, heart, liver, spleen, lung, kidney, intestine, stomach, bone marrow, and brain are taken. 100 µL of plasma is directly precipitated by adding 800 µL of acetonitrile, and the supernatant is frozen and centrifuged. 500 µL of the supernatant is blow dried with nitrogen, and 100 µL of the mobile phase is added for reconstitution, and injected for analysis. 0.1 g of the tissue is added with 1 mL of water and homogenized. The homogenate is treated following the treatment method for the plasma. The in vivo analysis results are shown in Table 6.

Effect of *bupleurum* root polysaccharides on in vivo distribution of Entecavir (ng/mL)

TABLE 6

Test result of Entecavir concentration (ng/L, n = 6)

| Group | Plasma | Liver | Spleen | Lung | Kidney | Heart | Stomach | Instine | Marrow |
|---|---|---|---|---|---|---|---|---|---|
| Entecavir | 30.6 | 26.8 | 28.4 | 26.3 | 27.5 | 26.14 | 25.6 | 24.3 | 18.9 |
| Entecavir + high dosage of *bupleurum* root polysaccharides | 23.3 | 35.4.5 | 18.3 | 24.6 | 23.6 | 18.9 | 19.8 | 18.2 | 13.4 |

It can be seen from the table above that *bupleurum* root polysaccharides can significantly increase the intra-hepatic distribution of Entecavir and reduce its concentration in other tissues, and expected to achieve an efficacy enhancing and toxicity reducing effect.

Example 13

The drug of the present invention enhances the inhibition of Tenofovir on the replication of HBV.

The drug of Example 7 is used.

The experiment is started with HepG2.215 cells that are grown to 80% confluence. The cells were assigned to 5 groups, comprising a blank control group, a treatment group with Tenofovir, a treatment group with Tenofovir in combination with high, medium, and low dosage of vinegar-baked *bupleurum* root polysaccharides. The concentration of Tenofovir is 0.8 µmol, the medium dosage of vinegar-baked *bupleurum* root polysaccharides is a corresponding dosage in Example 7, one-half of which is the low dosage, and twice of which is the high dosage. Culturing for 48 h after administration, the supernatant is collected, the expression of the HBV gene is determined by fluorescent quantitative PCR, and the HBsAg and HBeAg concentrations are determined by ELISA. The results are shown in Table 7.

TABLE 7

Effect of the preparation of the present invention on replication of HBV (normalization method, 100% for control group)

| | Blank control group | Tenofovir | Tenofovir + low dosage of PSS | Tenofovir + medium dosage of PSS | Tenofovir + high dosage of PSS |
|---|---|---|---|---|---|
| HBsAg | 100 | 33.2 ± 1.2 | 25.6 ± 2.5 | 14.6 ± 3.6 | 4.5 ± 2.7 |
| HBeAg | 100 | 39.8 ± 2.4 | 29.8 ± 2.1 | 18.7 ± 2.2 | 9.8 ± 2.3 |
| Expression of HBV gene | 100 | 45.2 ± 5.3 | 31.3 ± 3.6 | 19.2 ± 2.2 | 10.8 ± 2.4 |

As can be seen from the table above, the vinegar-baked *bupleurum* root polysaccharides can enhance the potency of Tenofovir against HBV, and are expected to increase the efficacy.

The above description of the detailed embodiments is only to illustrate the preferred implementation according to the present invention, and it is not to limit the scope of the present invention. Accordingly, all modifications and variations completed by those with ordinary skill in the art should fall within the scope of the present invention defined by the appended claims.

What is claimed is:

1. A pharmaceutical composition for treating hepatitis, liver fibrosis, and liver cancer, comprising the following components in parts by weight:
   0.15-10 parts of vinegar-baked *bupleurum* root polysaccharides or *bupleurum* root polysaccharides; and
   0.05-5 parts of matrine or Dipivoxil for treating hepatitis.

2. A pharmaceutical composition for treating hepatitis, liver fibrosis, and liver cancer according to claim 1, comprising the following components in parts by weight:
   0.05-2 parts of matrine; and
   0.5-5 parts of vinegar-baked *bupleurum* root polysaccharides or *bupleurum* root polysaccharides.

3. A pharmaceutical composition for treating hepatitis, liver fibrosis, and liver cancer according to claim 1, comprising the following components in parts by weight:
   0.05-1 part of matrine; and
   0.5-5 parts of vinegar-baked *bupleurum* root polysaccharides.

4. A pharmaceutical composition for treating hepatitis, liver fibrosis, and liver cancer according to claim 1, comprising the following components in parts by weight:
   0.010-0.1 part of Dipivoxil; and
   0.15-5 parts of vinegar-baked *bupleurum* root polysaccharides.

5. A pharmaceutical composition for treating hepatitis, liver fibrosis, and liver cancer according to claim 1, comprising the following components in parts by weight:
   0.05-2 parts of matrine; and
   0.84 part of vinegar-baked *bupleurum* root polysaccharides.

6. A traditional Chinese medicine preparation for treating hepatitis and liver cancer, comprising a therapeutically effective amount of a traditional Chinese medicine composition for treating hepatitis and liver cancer according to claim 1 and a pharmaceutically acceptable carrier.

* * * * *